United States Patent [19]
Harth et al.

[11] Patent Number: 5,693,340
[45] Date of Patent: Dec. 2, 1997

[54] DELAYED-RELEASE FORM FOR PHARMACEUTICAL ACTIVE COMPOUNDS

[75] Inventors: Klaus Harth, Altleiningen; Hartmut Hibst, Schriesheim; Juergen Dembowski, Goellheim; Reinhard Spengler, Ludwigshafen; Ernst Flaig, Heidelberg, all of Germany

[73] Assignee: BASF Aktiengesellschaft, Ludwigshafen, Germany

[21] Appl. No.: 727,314

[22] Filed: Oct. 8, 1996

Related U.S. Application Data

[63] Continuation of Ser. No. 154,428, Nov. 19, 1993, abandoned.

[30] Foreign Application Priority Data

Nov. 21, 1992 [DE] Germany ............ 42 39 244.6

[51] Int. Cl.$^6$ ............ A61K 9/16; A61K 9/30; A61K 9/32
[52] U.S. Cl. ............ 424/475; 424/468; 424/482; 424/490; 424/497
[58] Field of Search ............ 424/468, 459, 424/462, 475, 482, 490, 497, 474

[56] References Cited

U.S. PATENT DOCUMENTS

| | | | |
|---|---|---|---|
| 3,916,899 | 11/1975 | Theeuwes et al. | 128/260 |
| 5,000,886 | 3/1991 | Lawter et al. | 264/4.3 |
| 5,288,504 | 2/1994 | Versic | 424/497 |

FOREIGN PATENT DOCUMENTS

90/02546  3/1990  WIPO.

OTHER PUBLICATIONS

ASV. Low–Temp. Plasma Chem. Technol. Appl. Bd. 1, 1984, pp. 339–342, "Some Studies On Coating Of Activated Charcoal With Plasma Polymer Hexamethyldisiloxane", N. Hasirci et al.

*Primary Examiner*—Thurman K. Page
*Assistant Examiner*—James M. Spear
*Attorney, Agent, or Firm*—Oblon, Spivak, McClelland, Maier & Neustadt, P.C.

[57] ABSTRACT

A novel delayed-release form for pharmaceutical active compounds, characterized by a core containing the active compound and a diffusion-inhibiting, adhesive coating layer having a thickness in the range from 0.01 to 10 μm, consisting of a chemical network which has been applied to the support in a plasma-assisted chemical deposition process, and a process for its production are described.

13 Claims, No Drawings

DELAYED-RELEASE FORM FOR PHARMACEUTICAL ACTIVE COMPOUNDS

This application is a Continuation of application Ser. No. 08/154,428, filed on Nov. 19, 1993, now abandoned.

The invention relates to a novel, extremely thin delayed-release coating for solid pharmaceutical forms, which permits a hitherto unachieved accuracy in the adjustment of the active compound release rate.

In the treatment of diseases over a relatively long period of time, it is desirable to keep the frequency of administration of medicaments as low as possible. This improves the safety of treatment by avoiding irregular administrations, in that it stabilizes the active compound concentration present in the body and thus reduces the risk of undesired overdoses or insufficient doses. It moreover facilitates the treatment for the patient.

In many cases, therefore, preparation forms for the medicaments are sought which enable controlled release of the pharmaceutical active compound over a relatively long period of time. In the ideal case, such a delayed-release preparation should permit a delay in release which is accurately adjustable within wide limits and a high active compound content.

Various processes for preparing delayed-release preparations for the oral administration of medicaments are known.

In matrix tablets, the active compound is embedded in a matrix of suitable auxiliaries (cf. Ullmanns Encyklopädie der technischen Chemie [Ullmann's Encyclopedia of Industrial Chemistry], volume 18, Pharmaceutical Technologies). The active compound is slowly released from matrix tablets of this type by diffusion to the surface of the swollen and/or porous tablet body.

The delayed-release effect which can be achieved by embedding an active compound in a matrix is only controllable to a limited extent. The diffusion pathway, which increases with increasing time, in this case causes a release rate of the active compound which as a rule decreases according to an exponential function. The high content of the auxiliaries in the total amount of the matrix tablet moreover leads to a restriction of the amount of active compound which can be administered.

A delay in the release of active compound can also be achieved by a physicochemical binding of the active compound to a suitable support substance, such as biodegradable polymers or ion exchangers, the release rate being determined by the degradation of the support substance or the ion influx. As a rule, however, these systems are only suitable for active compounds administered in a relatively low dose.

A widespread process for preparing delayed-release forms is the lacquering of active compound-containing cores with suitable lacquers comprising e.g. the esters of acrylates and methacrylates or cellulose derivatives such as ethylcellulose. The release of active compound is controlled here by the diffusion of the medicament through the coating acting as the membrane.

Said lacquer coatings are customarily prepared (cf. Bauer-Lehmann-Osterwald-Rothgang, Überzogene Arzneiformen [Coated Pharmaceutical Forms], WVG, Stuttgart, 1988) by spraying on the lacquer layer in a rotating pan or a fluidized bed reactor and then drying. To apply the lacquer layer, both organic and aqueous solvents are used, both of which have specific disadvantages: organic solvents demand costly technical measures to avoid environmentally polluting emissions and to ensure occupational safety. Moreover, there is the risk with organic solvents of residues in the medicament, which can have toxic side effects as a consequence. Aqueous solvents are admittedly acceptable environmentally and with respect to toxic residues, but as a rule their use leads to a relatively poor homogeneity of the lacquer coating. In order to counteract an impairment of the delayed-release effect caused by this, an increase in the lacquer layer thickness therefore has to be accepted.

U.S. Pat. No. 3,916,899 describes a delayed-release form for active compounds, in which the active compound reservoir (e.g. in the form of a capsule) is surrounded by a semipermeable lacquer layer, which is impermeable to the active compound, but permeable to the particular liquid of the surrounding medium. The surrounding lacquer layer additionally contains a geometrically well-defined opening, by means of which the active compound dissolved in the surrounding liquid can pass outwards. After taking the delayed-release form, the digestive juices diffuse through the semipermeable lacquer layer into the interior of the capsule, the flow rate being controlled by the difference in osmotic pressure, which decreases through the lacquer layer, and by the permeability of the lacquer layer. The active compound in the interior of the capsule is continuously dissolved in the inflowing liquid and passes outwards through the geometric opening in the lacquer layer at a defined rate. With said osmotic system, however, depending on the capsule filling employed, local irritations of the tissue in the gastric or intestinal tracts can occur owing to an increased concentration. A part of the active compound as a rule additionally remains in the pharmaceutical form and is thus not available for the desired absorption. The preparation of said osmotic delayed-release forms is very complicated, since the lacquer layer of each individual capsule must be perforated by suitable methods, for example with the aid of a laser beam.

The object was therefore to find a novel, highly precise delayed-release form for pharmaceutical active compounds based on a diffusion-inhibiting coating having the following advantageous characteristics:

good delayed-release action even at low layer thicknesses (<1 μm)

highly precise release behavior which can be controlled via the layer thickness reproducible, homogeneous release behavior from pellet to pellet extensive dispensing with other pharmaceutical auxiliaries, so that very high active compound contents are made possible solvent-free, toxicologically acceptable, emission-free preparation process for the delayed-release layer.

The object is achieved in a delayed-release form and the process for its preparation as in the claims.

An important characteristic of the novel delayed-release form is the use of a thin coating layer inhibiting diffusion, which differs in construction, chemical composition, preparation and exactness of adjustability of the action very greatly from the previously known coatings inhibiting diffusion or dissolution.

The layers according to the invention have a very good diffusion-inhibiting action even at a layer thickness distinctly below 1 μm. A considerable reduction in the coating thickness compared with the prior art is thus achieved. The delayed-release layers according to the invention ensure a very homogeneous release of the active compound, which is linear as a function of time. Any desired delayed-release actions can thus be adjusted precisely in a simple manner by the choice of a suitable layer thickness. Great freedom exists here with respect to the nature and the shape of the active compound-containing particle. In particular, the delayed-release form according to the invention makes possible the use of highly concentrated active compound supports which ensure a particularly long-lasting release of active compound.

Important characteristics of the delayed-release layers according to the invention are, on the one hand, the special chemical composition of the layer, which is marked by a high degree of crosslinking, and, on the other hand, the novel preparation of the layer in a plasma-assisted chemical deposition process.

With respect to the chemical composition, it has been found that a particularly good delayed-release action is obtained if the delayed-release layer contains at least the elements Si and C, the content (based on the total amount of all elements without H) of silicon preferably being in the range from 1 to 40 atom % and of carbon being in the range from 60 to 99 atom %. The layer can also contain oxygen, nitrogen and, in particular, hydrogen. Small amounts of other elements do not, in general, interfere. Indispensable for achieving the desired inhibitory action is a strong chemical crosslinking of the C atoms, preferably the Si and C atoms of the layer. This crosslinking results in the Si atoms being characterized by a metallic type of bond and the C atoms simultaneously by a carbide type of bond even at relatively high O contents. The layers according to the invention thus differ significantly from other known diffusion-inhibiting layers, such as, for example, $SiO_2$ layers, in which the Si atoms have an oxide type of bond. Said character of the type of bond can be determined experimentally by ESCA (electron spectroscopy for chemical analysis) investigation of the layers.

An advantageous process found for the preparation of the delayed-release forms according to the invention was a special plasma-assisted chemical deposition of a mixture which contains organosilicon monomers.

Plasma-assisted vacuum processes for the production of thin layers have been known for a relatively long time (cf. R. F. Bhunshal et al., Deposition Technologies for Films and Coatings, Noyes Publications, 1982; H. Yasuda, Plasma Polymerization, Academic Press, Orlando, 1985) and are already used industrially in many areas, for example in the production of semiconductor components, of magnetic or optical data media or of wear-preventing layers for metallic tools. A distinction is as a rule made here between physical deposition processes (PVD processes, such as e.g. vapor deposition, sputtering or ion-plating), in which the starting material is present in condensed form, and chemical deposition processes (CVD processes), in which a suitable gaseous starting compound is introduced into the coating chamber, decomposed and in this case deposited in the form of a thin layer. The decomposition of the gaseous starting compound can be effected here either by the supply of thermal energy (thermal CVD) or by the action of a plasma (plasma-assisted CVD). Thermal CVD of gaseous monomers as a rule demands decomposition temperatures of several hundred degrees Celsius and is therefore not suitable for the coating of temperature-sensitive materials, such as pharmaceutical active compounds.

To date, several commercial applications of plasma-assisted PVD and CVD processes for the preparation of diffusion barrier layers are known, where, however, without exception extensive, as a rule, flat supports with surfaces which are as smooth as possible are coated. The known processes for diffusion barrier coating failed, however, until now in the coating of small three-dimensional supports with microscopically rough surfaces. Particular problems presented here were the adequate adhesion of the layer to the support material (in particular with high layer thicknesses), the homogeneity of the coating and the complete freedom from flaws of the layer. Attempts at diffusion barrier coating of active compound pellets with C-free (Si—O or Si—N) layers by reactive sputtering did not therefore produce the desired result: whereas with layer thicknesses below 250 nm no measurable delayed-release action was achieved, greater layer thicknesses led to an embrittlement of the coating layer with subsequent mechanical breakdown of the coating layer in the dissolution attempt. It was therefore all the more surprising that good delayed-release layers could be prepared by the process according to the invention even on microscopically rough surfaces of active compound pellets.

The process according to the invention is distinguished in that the active compound supports to be coated are agitated by mechanical or fluidic aids in a vacuum unit which contains a plasma device, a gas mixture which contains at least one organic compound being simultaneously admitted into the plasma field at given flow and pressure ratios. The organic compound can be an organosilicon compound or a hydrocarbon compound. The plasma conditions (flow and pressure) are adjusted such that a decomposition of the organic compound takes place in the plasma field with simultaneous formation of a network on the active compound supports. Suitable organo-silicon compounds are, for example, hexamethyldisiloxane, hexamethyldisilazane, tetraethyl orthosilicate, vinyltrimethylsilane and other methyl-, vinyl-, phenyl- or alkoxy-containing siloxanes, silazanes or silanes. A particularly preferred organosilicon compound is hexamethyldisiloxane. The gas mixture employed can moreover contain inert gases such as He, Ne, Ar, Kr or Xe, preferably Ar, as well as $O_2$ or $N_2$. A preferred flow rate of the mixture is in this case in the range from 1 to 10 000 sccm at a pressure in the range from $1\times10^{-3}$ to 100 mbar.

Either direct current (DC) or alternating current generators can be employed for the electrical supply of the plasma, the alternating current generators customarily working at 13.56 MHz (RF) or 2.45 GHz (microwave). The coupling of the DC voltage into the vacuum unit is effected in this case in a known manner (cf. eg. R. F. Bhunshah et al., Deposition Technologies for Films and Coatings, Noyes Publications, 1982) via a round, isolated electrode which is rod-like or provided with an otherwise suitable geometry, the remaining part of the vacuum unit being kept at ground potential. The coupling of the RF voltage is effected in a comparable manner, but for maximization of the coupled and for minimization of the reflected electrical power an electrical tuning unit (electrical network of coils and capacitors) between generator and electrode being used. The microwave excitation which can be alternatively used is effected in a known manner without electrodes, hollow or coaxial conductors being used outside the vacuum for supplying the electrical power. To couple the microwave into the plasma field, various arrangements are known, for example a horn aerial, which in the interior contains a quartz sheet as a vacuum seal. Alternatively, the microwaves can also be guided into the interior of the vacuum unit from an external hollow conductor with the aid of rod aerials, which are isolated and fixed in a vacuum-tight manner to a base plate. The plasma density in the vacuum range can in this case be additionally intensified in a known manner by means of magnetic fields, which as a rule leads to an increase in the charge carrier density and an increase in the coating rate.

In order to obtain a homogeneous coating and thus a uniform delayed-release action, it is necessary to keep the support materials to be coated, containing active compound or consisting of the active compound, in motion during the coating using suitable mechanical or fluidic devices. Suitable mechanical devices for this purpose are, for example, periodically agitated cages, drums, basins or troughs, in which the supports to be coated are stimulated to random motions. The mechanical device must in this case have suitable openings for the flow of the gaseous monomers and for the penetration of the plasma. It is alternatively possible that the supports to be coated are kept in random motion by means of a fluidized bed process.

For the achievement of a coating rate which is as high as possible and of a good homogeneity of the coating, an optimum overall arrangement of the gas inlet system, the plasma field and the agitation device for the active compound supports is important. When using flat electrodes having round or rectangular geometry, it is convenient in this case that the base surface of the agitation device, on which the active compound supports are mechanically activated, have a geometry similar to the electrode, so that the plasma field given by the shape of the electrode is utilized as effectively as possible. At the same time, the gas inlet system should ensure a homogeneous flow through the plasma field. When coupling the plasma by means of a round electrode, the use, for example, of one or more agitation devices lying one on top of the other and having a common central axis proves convenient. The gas supply is in this case effected in an advantageous manner at the level of each agitation device by means of a ring-shaped gas jet, whose internal diameter is chosen to be somewhat larger than the external diameter of the agitation device. The suction ratios of the pump system should in this case preferentially ensure a radial flow of the gas from the outer edge to the center of the agitation device.

The delayed-release layers according to the invention can be employed on active compound supports of very different nature and shape. Suitable active compound supports are granules, single crystals, also relatively compact crystal or powder particle agglomerates, especially pellets and in particular tablets. They consist of the pharmaceutical active compound, which also includes vitamins, or contain it in addition to a support and, if appropriate, other auxiliaries. Films can also be coated (for the purpose of transdermal administration) according to the invention.

Suitable pharmaceutical active compounds are any which are sufficiently soluble in the digestive juices to diffuse through the coating layer and to display their curative or preventive action in the body.

Pharmaceutical auxiliaries, which can be present in the core in addition to the active compound, are, for example, binders, lubricants, mold release agents, flow regulators and preservatives as well as fillers, softeners and antioxidants.

EXAMPLE 1

A fraction having a pellet diameter from 1.0 to 1.4 mm was selected from pellets of the active compound theophylline by sieving. The pellets were placed on an agitation device which consisted of a steel net having a mesh width of 0.4 mm, which was activated to vibrations by means of an electromagnetically driven shaking device.

The entire arrangement was introduced into a cylindrical vacuum unit, which was evacuated using a two-stage pump system (turbomolecular pump and rotary vane auxiliary pump) to a pressure of $10^{-6}$ mbar. A gas mixture of hexamethyldisiloxane (manufacturer: Merck, purity >99%) having a partial pressure of $2\times10^{-2}$ mbar and argon having a partial pressure of $1\times10^{-2}$ mbar was then admitted via a ring-shaped gas jet having an internal diameter of 150 mm. At constant suction power of the pump system, the flow rate of hexamethyldisiloxane was 35.8 sccm (standard cubic centimeters per minute).

A round steel electrode (diameter 150 mm) attached horizontally under the steel net at a distance of 56 mm was supplied with an alternating-current voltage of frequency 13.56 MHz with the aid of an RF generator. The power output of the RF generator was adjusted to 100 W, a potential of $-570$ V relative to a grounded reference point being established on the steel electrode. After a coating time of 14 min, the RF generator was switched off and the coating thus ended.

The coated pellets were subjected to a dissolution test in a paddle apparatus model USP XXI with a patch holder at a speed of 50 rpm and a temperature of 37° C. A pH of 1.2 was first established here in a test volume of 900 ml by addition of 0.08N hydrochloric acid. After a period of time of 2 h, the test medium was readjusted to a pH of 6.8 with the aid of the buffer addition method. To measure the concentration of the active compound released, a sample volume of 10 ml was taken hourly from the start, ie. even at pH 1.2, and the optical absorbance was measured at a wavelength of 270 nm with the aid of a spectrophotometer. The results of the dissolution test are shown in Tab. 1.

EXAMPLE 2

Coating as in Example 1, but coating time 56 min.

EXAMPLE 3

A fraction having a pellet diameter from 1.0 to 1.4 mm was selected from pellets of the active compound theophylline by sieving. The active compound supports were attached in a monolayer to a PET film using ethylcellulose, dissolved in an acetone/isopropanol mixture.

The film with the active compound supports was introduced into a cylindrical vacuum unit, which was evacuated using a two-stage pump system (turbomolecular pump and rotary vane auxiliary pump) to a pressure of $10^{-6}$ mbar. A gas mixture of hexamethyldisiloxane having a partial pressure of $2\times10^{-2}$ mbar and argon having a partial pressure of $1\times10^{-2}$ mbar was then admitted via a ring-shaped gas jet having an internal diameter of 150 mm. At constant suction power of the pump system, the flow rate of hexamethyldisiloxane was 35.8 sccm.

A round steel cathode (diameter 150 mm) attached centrally relative to the support film at a distance of 56 mm was supplied with an alternating-current voltage of frequency 13.56 MHz with the aid of an RF generator. The power output of the RF generator was adjusted to 100 W, a potential of $-480$ V relative to a grounded reference point being established on the steel electrode. After a coating time of 6 min 12 s, the RF generator was switched off and the coating thus ended.

The pellets coated in such a manner were subjected in the attached state to a dissolution test as in Example 1.

The results of the dissolution test are shown in Tab. 1.

EXAMPLE 4

As Example 3, but coating time 12 min 24 s.

EXAMPLE 5

As Example 3, but coating time 49 min 38 s.

TABLE 1

| Dissolution time [h] | Comparison sample (uncoated) | Amount of active compound released [%] Examples | | | | |
|---|---|---|---|---|---|---|
| | | 1 | 2 | 3 | 4 | 5 |
| 0 | 0 | 0 | 0 | 0 | 0 | 0 |
| 1 | 98.4 | 67.5 | 17.3 | 8.4 | 3.5 | 0.4 |
| 2 | 99.5 | 84.5 | 28.3 | 19.6 | 8.8 | 2.4 |
| 3 | 100 | 90.0 | 36.8 | 30.6 | 13.4 | 3.0 |
| 4 | 100 | 93.5 | 43.9 | 42.1 | 19.6 | 4.0 |
| 5 | 100 | 95.2 | 50.2 | 50.7 | 25.1 | 5.5 |
| 6 | 100 | 96.7 | 55.6 | 59.9 | 29.5 | 6.2 |
| 7 | 100 | 98.2 | 60.3 | 70.8 | 35.1 | 7.6 |
| 8 | 100 | 98;3 | 63.8 | 77.2 | 40.5 | 9.0 |

We claim:

1. A delayed-release form of a water-soluble, solid pharmaceutically active compound, comprising a core comprised of said pharmaceutically active compound, said core being coated with at least one pharmaceutically acceptable, diffusion-inhibiting, adhesive coating layer, said coating layer comprising a chemical network having a thickness in the range from 0.01 to 10 µm, said network having carbon atoms, or carbon and silicon atoms, in chemically crosslinked relation, said network having been deposited by a plasma-assisted chemical deposition process of an organic non-polymer compound.

2. A delayed-release form as claimed in claim 1, wherein the coating layer contains at least the elements silicon and carbon, the Si content of the coating layer being in the range from 1 to 40 atom % and the C content in the range from 60 to 99 atom % (in each case based on the total content of all elements apart from hydrogen).

3. A delayed-release form as claimed in claim 1, wherein the core consists of granules, an agglomerate or a crystal of the active compound.

4. A delayed-release form as claimed in claim 1, wherein the core consists of a pellet which contains the active compound and pharmaceutical auxiliaries.

5. A delayed-release form of a water-soluble, solid pharmaceutically active compound, comprising a core comprised of said pharmaceutically active compound, said core being coated with at least one pharmaceutically acceptable, diffusion-inhibiting, adhesive coating layer, said coating layer comprising a chemical network having a thickness in the range from 0.01 to 10 µm, said network having carbon atoms, or carbon and silicon atoms, in chemically crosslinked relation, said network having been deposited by a plasma-assisted chemical deposition of an non-polymer organic compound.

6. The delayed-release pharmaceutical form of claim 5, wherein said organic compound is a hydrocarbon.

7. The delayed-release pharmaceutical form of claim 5, wherein said organic compound is an organosilicon compound.

8. A delayed-release form of a water-soluble, solid pharmaceutically active compound, comprising a core comprised of said pharmaceutically active compound, said core being coated with at least one pharmaceutically acceptable, diffusion-inhibiting, adhesive coating layer, said coating layer comprising a chemical network having a thickness in the range from 0.01 to 10 µm, said network having carbon atoms, or carbon and silicon atoms, in chemically crosslinked relation, said network having been deposited by a plasma-assisted chemical deposition process of an organic non-polymer compound, said core consisting of a tablet which contains the active compound and pharmaceutical auxiliaries.

9. A process for preparing a delayed-release form of a water-soluble, solid pharmaceutically active compound, comprising a core comprised of said pharmaceutically active compound, said core being coated with at least one pharmaceutically acceptable, diffusion-inhibiting, adhesive coating layer, said coating layer comprising a chemical network having a thickness in the range from 0.01 to 10 µm, said network having carbon atoms, or carbon and silicon atoms, in chemically crosslinked relation, said network having been deposited by a plasma-assisted chemical deposition of an organic compound; said process comprising producing the diffusion-inhibiting coating layer by plasma-assisted decomposition of a gas mixture which contains at least one organic compound in a closed volume with deposition and simultaneous network formation on the active compound supports, which are kept in motion.

10. A preparation process as claimed in claim 9 wherein the gas mixture contains at least one organosilicon compound.

11. A preparation process as claimed in claim 10, wherein the organosilicon compound used is hexamethyldisiloxane.

12. A preparation process as claimed in claim 9, wherein the flow rate is set in the range from 1 to 10,000 sccm at a pressure in the range from $1 \times 10^{-3}$ to 100 bar.

13. A delayed-release form of a water soluble, solid pharmaceutically active compound as set forth in claim 8 wherein the chemical network of said coating layer is composed of carbon and silicon atoms in chemically crosslinked relation.

* * * * *